United States Patent [19]

Imhof et al.

[11] Patent Number: 4,764,522
[45] Date of Patent: Aug. 16, 1988

[54] ETHYLENEDIAMINE MONOAMIDES

[75] Inventors: René Imhof, Gipf-Oberfrick; Emilio Kyburz, Reinach, both of Switzerland

[73] Assignee: Hoffmann-La Roche Inc., Nutley, N.J.

[21] Appl. No.: 766,364

[22] Filed: Aug. 16, 1985

[30] Foreign Application Priority Data

Aug. 29, 1984 [CH] Switzerland .......... 4132/84
Jun. 5, 1985 [CH] Switzerland .......... 2404/85

[51] Int. Cl.$^4$ .......... A61K 31/44; C07D 213/81; C07D 261/18; C07D 277/56
[52] U.S. Cl. .......... 514/354; 514/346; 514/352; 514/365; 514/374; 546/291; 546/308; 546/309; 546/323; 548/200; 548/248; 548/235; 544/406; 549/72; 549/487
[58] Field of Search .......... 546/323, 291, 309, 308; 544/406; 548/248, 200, 235; 549/72, 487; 514/256, 354, 365, 374, 378, 448, 471, 346, 352

[56] References Cited

U.S. PATENT DOCUMENTS 4,034,106 7/1977 Smith .......... 514/522

FOREIGN PATENT DOCUMENTS 2655233 6/1977 Fed. Rep. of Germany .
451304 8/1936 United Kingdom .

OTHER PUBLICATIONS

CA 99:157898r Marsham et al.; 1983.
CA 99:212539b Barlow et al.; 1983.
CA 71 81421d Cragoe et al.; 1909.
CA 74;53846g Gragoe et al.; 1971.
CA 41:1947,1325f
CA 96:162116b 1982.
CA 96:161957q Sitzius et al.; 1982.
CA 86:135937e Schubert et al.; 1977.
CA 97:182347b Large et al.; 1982.
CA 84:135281x Smith; 1976.

Primary Examiner—Mary C. Lee
Assistant Examiner—Dale A. Bjorkman
Attorney, Agent, or Firm—Jon S. Saxe; Bernard S. Leon; Matthew Boxer

[57] ABSTRACT

Compounds of the formula

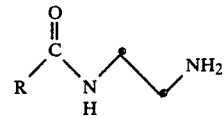

I wherein R is an aromatic, 5- or 6-membered heterocyclic residue, as described herein, and their pharmaceutically usable acid additions salts are described. These compounds have interesting monoamine oxidase inhibiting properties with low toxicity and can accordingly be used for the treatment of depressive states and parkinsonism.

17 Claims, No Drawings

ETHYLENEDIAMINE MONOAMIDES

BRIEF SUMMARY OF THE INVENTION

The invention is concerned with ethylenediamine monoamide derivatives. In particular, it is concerned with ethylenediamine monoamides of the formula

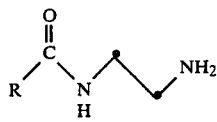   I wherein R is

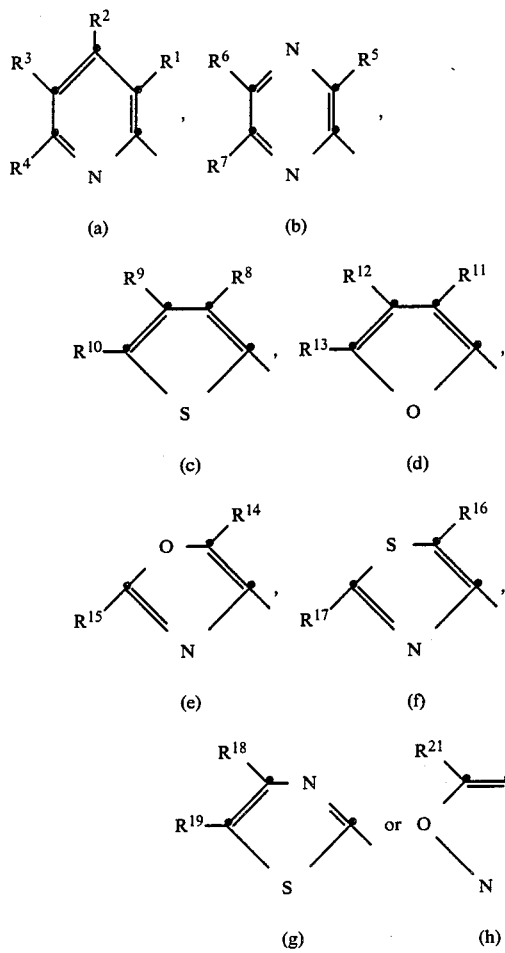

in which at least two of the substituents $R^1$, $R^2$, $R^3$ and $R^4$ are hydrogen and the remaining two each independently are hydrogen, halogen, nitro, amino, hydroxy, lower-alkoxy, lower-alkyl or optionally substituted phenyloxy or phenylmethyloxy, $R^5$, $R^6$ and $R^7$ each independently are hydrogen or halogen, $R^8$, $R^9$ and $R^{10}$ each independently are hydrogen, halogen or lower-alkyl, with the proviso that at least one of $R^8$, $R^9$ and $R^{10}$ is different from hydrogen, $R^{11}$, $R^{12}$ and $R^{13}$ each independently are hydrogen or halogen, with the proviso that at least one of $R^{11}$, $R^{12}$ and $R^{13}$ is different from hydrogen, $R^{14}$, $R^{15}$, $R^{16}$, $R^{18}$ and $R^{19}$ each independently are hydrogen, halogen or lower-alkyl, $R^{17}$ is hydrogen or halogen and $R^{20}$ and $R^{21}$ each independently are hydrogen or lower-alkyl, and pharmaceutically usable acid addition salts thereof. The compounds of formula I are useful in the control or prevention of depressive state and parkinsonism.

DETAILED DESCRIPTION OF THE INVENTION

The term "lower-alkyl" used in this description denotes straight-chain and branched hydrocarbon residues with 1–3 carbon atoms, i.e. methyl, ethyl, n-propyl and isopropyl. The term "lower-alkoxy" denotes lower alkyl ether groups in which the term "lower-alkyl" is as described above. The term "halogen" denotes the four halogens fluorine, chlorine, bromine and iodine. The term "substituted phenyl" in substituted phenyloxy or phenylmethyloxy denotes a phenyl residue in which one or more of the hydrogen atoms is/are substituted by halogen, lower-alkyl, lower-alkoxy, nitro or hydroxy. The term "leaving group" denotes known groups such as halogen, preferably chlorine or bromine, arylsulfonyloxy such as, for instance, tosyloxy, alkylsulfonyloxy such as, for instance, mesyloxy, and the like.

The term "pharmaceutically usable acid addition salts" denotes salts with inorganic and organic acids such as, for example, hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like. Such salts can be manufactured readily by any person skilled in the art having regard to the state of the art and bearing in mind the nature of the compound to be converted into a salt.

The invention is concerned with ethylenediamine monoamide derivatives. In particular, it is concerned with ethylenediamine monoamides of the formula

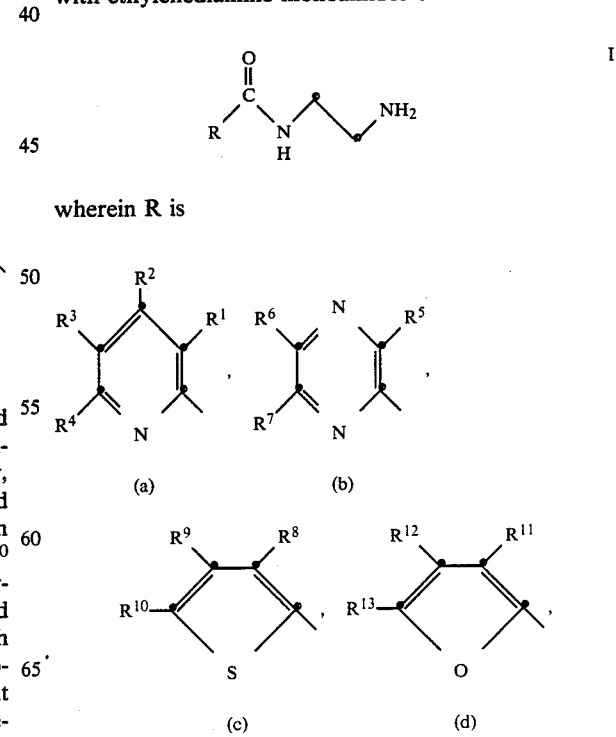   I wherein R is

-continued

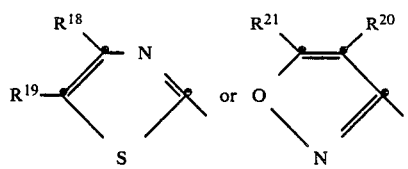

(e)   (f)

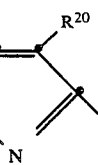

(g)   (h)

in which at least two of the substituents $R^1$, $R^2$, $R^3$ and $R^4$ are hydrogen and the remaining two each independently are hydrogen, halogen, nitro, amino, hydroxy, lower-alkoxy, lower-alkyl or optionally substituted phenyloxy or phenylmethyloxy, $R^5$, $R^6$ and $R^7$ each independently are hydrogen or halogen, $R^8$, $R^9$ and $R^{10}$ each independently are hydrogen, halogen or lower-alkyl, with the proviso that at least one of $R^8$, $R^9$ and $R^{10}$ is different from hydrogen, $R^{11}$, $R^{12}$ and $R^{13}$ each independently are hydrogen or halogen, with the proviso that at least one of $R^{11}$, $R^{12}$ and $R^{13}$ is different from hydrogen, and $R^{14}$, $R^{15}$, $R^{16}$, $R^{18}$ and $R^{19}$ each independently are hydrogen, halogen or lower-alkyl, $R^{17}$ is hydrogen or halogen and $R^{20}$ and $R^{21}$ each independently are hydrogen or lower-alkyl, and pharmaceutically usable acid addition salts thereof.

U.S. Pat. No. 4,034,106, generically discloses certain of the compounds of formula I, but does not specifically disclose any compounds of formula Ia below. Moreover, compounds of formula I have surprisingly been found to possess interesting and therapeutically usable pharmacodynamic properties with low toxicity. Thus, in animal experiments it has been found that the compounds of formula I above and their pharmaceutically usable acid addition salts have monoamine oxidase (MAO) inhibiting properties.

Objects of the invention are compounds of formula I and their pharmaceutically usable acid addition salts as therapeutically active substances, medicaments containing a compound of formula I or a pharamceutically usable acid addition salt thereof, the manufacture of such medicaments and the use of compounds of formula I and their pharmaceutically usable acid addition salts in the control or prevention of illnesses or in the improvement of health, especially in the control or prevention of depressive states and parkinsonism.

With the exception of N-(2-aminoethyl)pyridine-2-carboxamide described in Acta Polon. Pharm. 39, 41 (1982) the compounds of formula I, i.e. the ethylenediamine monoamide derivatives of the formula

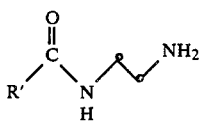

Ia wherein R' is

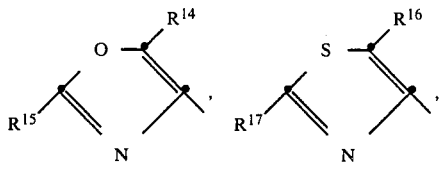

(a')   (b)

(c)   (d)

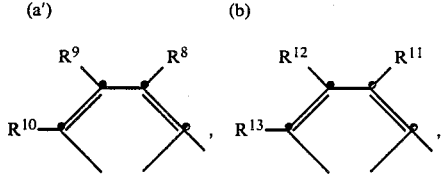

(e)   (f)

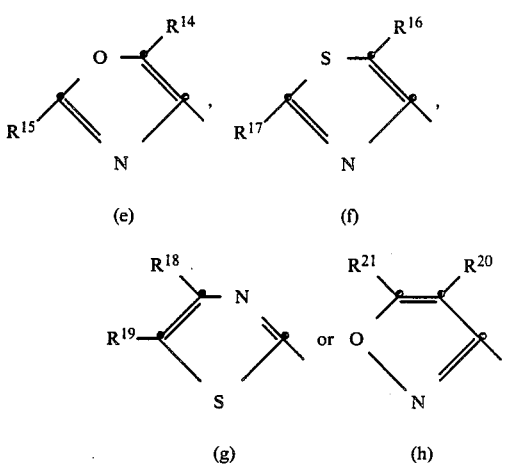

(g)   (h)

in which at least two of the substituents $R^{1'}$, $R^{2'}$, $R^{3'}$ and $R^{4'}$ are hydrogen and the remaining two each independently are hydrogen, halogen, nitro, amino, hydroxy, lower-alkoxy, lower-alkyl or optionally substituted phenyloxy or phenylmethyloxy, with the proviso that $R^{1'}$, $R^{2'}$, $R^{3'}$ and $R^{4'}$ are not simultaneously hydrogen, $R^5$, $R^6$ and $R^7$ each independently are hydrogen or halogen, $R^8$, $R^9$ and $R^{10}$ each independently are hydrogen, halogen or lower-alkyl, with the proviso that at least one of $R^8$, $R^9$ and $R^{10}$ is different from hydrogen, $R^{11}$, $R^{12}$ and $R^{13}$ each independently are hydrogen or halogen, with the proviso that at least one of $R^{11}$, $R^{12}$ and $R^{13}$ is different from hydrogen, $R^{14}$, $R^{15}$, $R^{16}$, $R^{18}$ and $R^{19}$ each independently are hydrogen, halogen or lower-alkyl, $R^{17}$ is hydrogen or halogen and $R^{20}$ and $R^{21}$ each independently are hydrogen or lower-alkyl, and their acid addition salts are novel and are an object of the invention.

A final object of the invention is a process for the manufacture of the compounds of formula Ia above and their pharmaceutically usable acid addition salts.

Preferred compounds of formula I are those in which R is the group (a), (f), (g) or (h).

Those compounds of formula I in which at least three of the substituents $R^1$, $R^2$, $R^3$ and $R^4$ are hydrogen and the fourth substituent is hydrogen, halogen, amino, hydroxy or lower-alkoxy are especially preferred.

Those compounds of formula I in which one of the substituents $R^{16}$ and $R^{17}$ or $R^{18}$ and $R^{19}$ is hydrogen and the other substituent is hydrogen or halogen are also especially preferred.

From the above it follows that of the compounds of formula I there are especially preferred those in which R is one of the groups (a), (f), (g) and (h), at least three of the substituents $R^1$, $R^2$, $R^3$ and $R^4$ are hydrogen and the fourth substituent is hydrogen, halogen, amino, hydroxy or lower-alkoxy, one of the substituents $R^{16}$ and $R^{17}$ or $R^{18}$ and $R^{19}$ is hydrogen and the other substituent is hydrogen or halogen.

Particularly preferred compounds of formula I are:
N-(2-aminoethyl)-4-methoxypyridine-2-carboxamide,
N-(2-aminoethyl)thiazole-2-carboxamide,
N-(2-aminoethyl)-4-bromopyridine-2-carboxamide,
N-(2-aminoethyl)-4-chloropyridine-2-carboxamide,
N-(2-aminoethyl)-2-chlorothiazole-4-carboxamide,
N-(2-aminoethyl)-5-methylisoxazole-3-carboxamide,
N-(2-aminoethyl)-6-bromopyridine-2-carboxamide,
N-(2-aminoethyl)-6-chloropyridine-2-carboxamide,
N-(2-aminoethyl)-5-bromothiazole-4-carboxamide,
N-(2-aminoethyl)-3-aminopyridine-2-carboxamide,
N-(2-aminoethyl)pyridine-2-carboxamide and
N-(2-aminoethyl)-5-chloropyridine-2-carboxamide.

The compounds of formula Ia and their pharmaceutically usable acid addition salts can be manufactured in accordance with the invention by (a) reacting a compound of the formula $$\underset{R'}{\diagup}\overset{O}{\underset{\|}{C}}-OH \qquad II$$

wherein R' is as described above, in the form of the free acid or in the form of a reactive functional derivative thereof with ethylenediamine, or (b) reacting a compound of the formula $$\underset{R'}{\diagup}\overset{O}{\underset{\|}{C}}\diagdown\underset{\underset{R^{22}}{|}}{N}\diagdown R^{23} \qquad III$$

wherein R' is as described above, $R^{22}$ is hydrogen and $R^{23}$ is a leaving group, with ammonia, or (c) converting the residue $R^{24}$ in a compound of the formula $$\underset{R'}{\diagup}\overset{O}{\underset{\|}{C}}\diagdown\underset{H}{N}\diagdown R^{24} \qquad IV$$

wherein R' is as described above and $R^{24}$ is a residue convertible into an amino group, into the amino group, or (d) cleaving off the phenylmethyl group in a compound of the formula $$\text{Ib}$$

wherein at least two of the substituents $R^{2''}$, $R^{3''}$ and $R^{4''}$ are hydrogen and the third is hydrogen, halogen, nitro, amino, hydroxy, lower-alkoxy, lower-alkyl or optionally substituted phenyloxy and $R^{1''}$ is phenylmethyloxy, and, if desired, converting a compound obtained into a pharmaceutically usable acid addition salt.

As reactive functional derivatives of the acids of formula II there come into consideration, for example, halides, e.g. chlorides, symmetric or mixed anhydrides, esters, e.g. methyl esters, p-nitrophenyl esters or N-hydroxysuccinimide esters, azides and amides, e.g. imidazolides or succinimides.

The reaction of an acid of formula II or a reactive functional derivatives thereof with ethylenediamine according to variant (a) of the above process can be carried out according to conventional methods. Thus e.g. a free acid of formula II can be reacted with ethylenediamine in the presence of a condensation agent in an inert solvent. If a carbodiimide such as dicyclohexylcarbodiimide is used as the condensation agent, then the reaction is conveniently carried out in an alkanecarboxylic acid ester such as ethyl acetate, an ether such as tetrahydrofuran or dioxane, a chlorinated hydrocarbon such as methylene chloride or chloroform, an aromatic hydrocarbon such as benzene, toluene or xylene, acetonitrile or dimethylformamide at a temperature between about −20° C. and room temperature, preferably at about 0° C. If phosphorus trichloride is used as the condensation agent, then the reaction is conveniently carried out in a solvent such as pyridine at a temperature between about 0° C. and the reflux temperature of the reaction mixture. In another embodiment of variant (a) ethylenediamine is reacted with one of the aforementioned reactive functional derivatives of an acid of formula II. Thus e.g. a halide, e.g. the chloride, of an acid of formula II can be reacted at about 0° C. with ethylenediamine in the presence of a solvent such as diethyl ether.

The compounds of formula III are, for example, N-(2-haloethyl)carboxamides such as N-(2-chloroethyl)carboxamides, N-(2-methylsulfonylethyl)carboxamides or N-(2-p-toluenesulfonylethyl)carboxamides and the like.

In accordance with variant (b) a compound of formula III can be reacted in a manner known per se with ammonia at a temperature between about −40° C. and 50° C., if desired in the presence of a solvent such as dimethylformamide, dimethylacetamide, dimethyl sulfoxide and the like. The reaction is conveniently carried out in the presence of a solvent at about room temperature.

The conversion of the residue $R^{24}$ into amino in accordance with variant (c) is also carried out in a manner known per se depending on the nature of the residue $R^{24}$. If this is an amide, then the conversion is conveniently carried out by acidic or basic hydrolysis. The acidic hydrolysis is advantageously carried out using a solution of a mineral acid such as hydrochloric acid, aqueous hydrogen bromide, sulfuric acid, phosphoric acid and the like in an inert solvent such as an alcohol, e.g. methanol or ethanol, or an ether, e.g. tetrahydrofuran or dioxane. The basic hydrolysis can be carried out using aqueous solutions of alkali metal hydroxides such as potassium hydroxide solution or sodium hydroxide solution. Inert organic solvents such as those mentioned above in connection with the acidic hydrolysis can be added as solubilizers. The acidic and basic hydrolysis can be carried out in a temperature range of about room temperature to the reflux temperature, with the boiling point of the reaction mixture or a temperature slightly thereunder being preferred. If $R^{24}$ is phthalimido, then this can be converted into the amino group not only by acidic and basic hydrolysis, but also by aminolysis with an aqueous solution of a lower alkylamine such as methylamine or ethylamine. A lower alkanol such as ethanol can be used as the organic solvent. This reaction is preferably carried out at room temperature. A third method for the conversion of phthalimido into amino comprises reacting compounds of formula IV in which $R^{24}$ is phthalimido with hydrazine in an inert solvent such as ethanol, a mixture of ethanol and chloroform, tetrahydrofuran or agueous ethanol. The reaction temperature can be varied in a range of about room temperature up to about 100° C., with the boiling point of the chosen solvent being preferred. The resulting product can be extracted with dilute mineral acid and can subsequently be obtained by making the acidic solution basic. The t-butoxycarbonylamino residue is conveniently converted into the amino group using trifluoroacetic acid or formic acid in the presence or absence of an inert solvent at about room temperature, while the conversion of the trichloroethoxycarbonylamino group into the amino group is carried out using zinc or cadmium under acidic conditions. The acidic conditions are conveniently achieved by carrying out the reaction in acetic acid in the presence or absence of an additional inert solvent such as an alcohol, e.g. methanol. The benzyloxycarbonylamino residue can be converted into the amino group in a known manner by acidic hydrolysis as described above or hydrogenolytically. If $R^{24}$ is azido, then the azido group can be reduced to the amino group according to known methods, for example with elementary hydrogen in the presence of a catalyst such as palladium/carbon. Raney-nickel platinum oxide and the like. If $R^{24}$ is hexamethylenetetraammonium, then the hexamethylenetetraammonium group can be converted into the amino group by acidic hydrolysis according to methods which are likewise known.

The cleavage of the phenylmethyl group in accordance with variant (d) is carried out according to methods known per se, conveniently by hydrogenolysis in the presence of palladium at room temperature or by hydrolysis with trifluoroacetic acid in the presence or absence of an inert solvent at a temperature between about room temperature and 100° C., preferably at about 50° C.

The compounds of formula II and their reactive functional derivatives used as starting materials in variant (a) are known or can be obtained in analogy to the preparation of the known compounds.

The compounds of formula III used as starting materials in variant (b) are also known or are analogues of known compounds and can be prepared in a manner known per se. Thus, for example, a compound of formula II or a reactive functional derivative thereof can be reacted with ethanolamine under the reaction conditions given for variant (a) and the N-(2-hydroxyethyl)-carboxamide obtained can be converted into the desired compound of formula III in a manner known per se, e.g. by reaction with a halogenating agent such as phosphorus trichloride, phosphorus tribromide, phosphorus pentachloride, phosphorus oxychloride and the like, an arylsulfonyl halide such as tosyl chloride or an alkylsulfonyl halide such as mesyl chloride.

The compounds of formula IV used as starting materials in variant (c) are also known or are analogues of known compounds and can be prepared in a manner known per se. Thus, for example, a compound of formula II or a reactive functional derivative thereof can be reacted with a compound of the formula

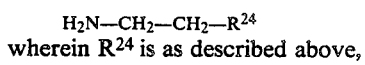

wherein $R^{24}$ is as described above, under the reaction conditions given for variant (a). The compounds of formula V are known or can be obtained in analogy to the preparation of the known compounds.

In accordance with an alternative process the compounds of formula IV in which $R^{24}$ is phthalimido, azido or hexamethylenetetraammonium can also be obtained by reacting a compound of formula III with potassium phthalimide, an alkali metal azide or hexamethylenetetraamine. The reaction is carried out in a manner known per se under the reaction conditions given for variant (b).

The compounds of formula Ib used as starting materials in variant (d) fall under formula Ia and can accordingly be obtained according to the methods described for the preparation of these compounds.

As mentioned above, the compounds of formula I and their pharmaceutically usable acid addition salts have monoamine oxidase (MAO) inhibiting activity. On the basis of this activity the compounds of formula I and their pharmaceutically usable acid addition salts can be used for the treatment of depressive states and parkinsonism.

The MAO inhibiting activity of the compounds in accordance with the invention can be determined using standard methods. Thus, the substances to be tested were administered p.o. to rats. Two hours thereafter the animals were killed and the MAO inhibiting activity was measured in homogenates of the brain according to the method described in Biochem. Pharmacol. 12 (1963) 1439–1441, but using phenethylamine ($2.10^{-5}$ mol.$1^{-1}$) in place of tyramine as the substrate. The thus-determined activity of some compounds in accordance with the invention as well as their toxicity are evident from the following $ED_{50}$ values ($\mu$mol/kg, p.o. in the rat) and $LD_{50}$ values (mg/kg, p.o. in the mouse), respectively:

| Compound | $ED_{50}$ | $LD_{50}$ |
| --- | --- | --- |
| N—(2-Aminoethyl)-4-bromopyridine-2-carboxamide hydrochloride | 4 | 1000–2000 |
| N—(2-Aminoethyl)-4-chloropyridine-2-carboxamide hydrochloride | 5 | 1250–2500 |
| N—(2-Aminoethyl)-2-chlorothiazole-4-carboxamide hydrochloride | 6 | 2500–5000 |
| N—(2-Aminoethyl)-5-methylisoxazole-3-carboxamide hydrochloride | 20 | >4000 |
| N—(2-Aminoethyl)-6-bromopyridine-2-carboxamide hydrochloride | 8 | 1000–2000 |
| N—(2-Aminoethyl)-6-chloropyridine-2-carboxamide hydrochloride | 10 | 625–1250 |
| N—(2-Aminoethyl)-5-bromothiazole- | 10 | 1250–2500 |

| Compound | ED$_{50}$ | LD$_{50}$ |
|---|---|---|
| 4-carboxamide hydrochloride N—(2-Aminoethyl)-3-aminopyridine-2-carboxamide dihydrochloride | 5 | 2500–5000 |
| N—(2-Aminoethyl)pyridine-2-carboxamide dihydrochloride | 1.7 | >4000 |
| N—(2-Aminoethyl)-5-chloropyridine-2-carboxamide hydrochloride | 0.161 | 1000–2000 |

The compounds of formula I and their pharmaceutically usable acid addition salts can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be carried out rectally, e.g. in the form of suppositories, or parenterally, e.g. in the form of injection solutions.

For the manufacture of tablets, coated tablets, dragees and hard gelatine capsules the compounds of formula I and their pharmaceutically usable acid addition salts can be processed with pharmaceutically inert, inorganic or organic excipients. As such excipients there can be used e.g. for tablets, dragees and hard gelatine capsules lactose, maize starch or derivatives thereof, talc, stearic acid or its salts etc. For soft gelatine capsules there are suitable as excipients e.g. vegetable oils, waxes, fats, semi-solid and liquid polyols etc.

For the manufacture of solutions and syrups there are suitable as excipients e.g. water, polyols, saccharose, invert sugar, glucose etc.

For injection solutions there are suitable as excipients e.g. water, alcohols, polyols, glycerine, vegetable oils etc.

For suppositories there are suitable as excipients e.g. natural or hardened oils, waxes, fats, semi-liquid or liquid polyols etc.

Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

In accordance with the invention compounds of the formula I as well as their pharmaceutically usable acid addition salts can be used in the control or prevention of depressive states and parkinsonism. Compounds of formula I are administered to a warm-blooded animal in need of such treatment. The dosage can vary within wide limits and is, of course, fitted to the individual requirements in each particular case. In general, in the case of oral administration a daily dosage of about 10 to 100 mg of a compound of formula I should be appropriate, although the upper limit given above can also be exceeded should this be found to be indicated.

The following Examples are intended to illustrate the present invention, but they are not intended to be limiting in any manner. All temperatures are given in degrees Celsius.

EXAMPLE 1

To a suspension of 24.6 g of 2-pyridinecarboxylic acid and 19.9 ml of ethyl chloroformate in 250 ml of methylene chloride was added dropwise at 0° internal temperature 42 ml of triethylamine. After completion of the addition (1 hour), there was added dropwise thereto at 0°–5° a solution of 22.4 g of monoacetylethylenediamine in 50 ml of methylene chloride. The reaction mixture was stirred at 5° for a further 30 minutes and thereafter adjusted to pH 2 at 0° with 37% hydrochloric acid. The reaction mixture was filtered, the acidic, aqueous phase was separated and washed twice with 200 ml of methylene chloride each time.

The aqueous phase was thereafter made alkaline with sodium hydroxide solution and extracted several times with methylene chloride. The methylene chloride extracts were dried over magnesium sulfate and concentrated. The residue was recrystallized from ethyl acetate. There was obtained N-(2-acetaminoethyl)-2-pyridinecarboxamide, m.p. 96°–99°.

12.0 g of N-(2-acetaminoethyl)-2-pyridine-carboxamide were suspended in 100 ml of alcohol and 116 ml of 2N hydrochloric acid and the suspension was heated to reflux overnight. The reaction mixture was thereafter concentrated under reduced pressure, the solid residue (13.4 g) was boiled up with methanol, cooled, suction filtered and dried. There was obtained N-(2-aminoethyl)-pyridine-2-carboxamide dihydrochloride as white crystals, m.p. 262° (dec.).

The monoacetylethylenediamine was prepared according to J. Hill et al. JACS 61 (1939), 822, b.p. 124°–127°/4 Pa.

EXAMPLE 2

6.0 g of 4-nitro-2-pyridinecarboxylic acid were stirred at 60° bath temperature for 4 hours in 300 ml of absolute tetrahydrofuran and 5.9 g of 1,1'-carbonyldiimidazole. Thereafter, 6.0 g of t-butyl (2-aminoethyl)-carbamate were added thereto and the mixture was heated to reflux for 4 hours. The reaction mixture was concentrated under reduced pressure and thereafter partitioned between ethyl acetate and water. The combined organic phases were dried over magnesium sulfate and concentrated. The residue was crystallized from ethyl acetate, whereby there was obtained t-butyl [2-(4-nitropyridine-2-carboxamido)ethyl]carbamate as white crystals, m.p. 130°–131°.

In an analogous manner to that described above,
starting from 4.0 g of 5-nitro-2-pyridinecarboxylic acid there was obtained t-butyl [2-(5-nitropyridine-2-carboxamido)ethyl]carbamate, m.p. 141°–142°;
starting from 4.0 g of 4-bromo-2-pyridinecarboxylic acid there was obtained t-butyl [2-(4-bromopyridine-2-carboxamido)ethyl]carbamate, m.p. 134°;
starting from 8.0 g of 5-bromo-2-pyridinecarboxylic acid there was obtained t-butyl [2-(5-bromopyridine-2-carboxamido)ethyl]carbamate, m.p. 118°;
starting from 16.0 g of 6-bromo-2-pyridinecarboxylic acid there was obtained t-butyl [2-(6-bromopyridine-2-carboxamido)ethyl]carbamate, m.p. 108°–109°.
starting from 10.0 g of 6-chloro-2-pyridinecarboxylic acid there was obtained t-butyl [2-(6-chloropyridine-2-carboxamido)ethyl]carbamate, m.p. 114°–115°.
starting from 1.4 g of 4,6-dichloro-2-pyridinecarboxylic acid there was obtained t-butyl [2-(4,6-dichloropyridine-2-carboxamido)ethyl]carbamate, m.p. 126°–127°.
starting from 5.9 g of a mixture of 3-chloro-5-benzyloxy-2-pyridinecarboxylic acid and 5-chloro-3-benzyloxy-2-pyridinecarboxylic acid and subsequent chromatography of the mixture on silica gel there was obtained t-butyl[2-(3-chloro-5-benzyloxy-2-carboxamido)ethyl]carbamate, m.p. 127°–130° and t- butyl [2-(5-chloro-3-benzyloxy-2-carboxamido)ethyl]carbamate, m.p. 130°-133°;

starting from 1.6 g of 3-methoxy-2-pyridinecarboxylic acid there was obtained t-butyl [2-(3-methoxypyridine-2-carboxamido)ethyl]carbamate, m.p. 115°;

starting from 3.7 g of 4-methoxy-2-pyridinecarboxylic acid there was obtained t-butyl [2-(4-methoxypyridine-2-carboxamido)ethyl]carbamate, m.p. 106°-107°;

starting from 28.2 of 6-methyl-2-pyridinecarboxylic acid there was obtained t-butyl [2-(6-methylpyridine-2-carboxamido)ethyl]carbamate, m.p 94°-95°;

starting from 6.8 g of oxazole-4-carboxylic acid there was obtained t-butyl [2-(oxazole-4-carboxamido)ethyl]carbamate, m.p. 148°-150°;

starting from 9.8 g of thiazole-4-carboxylic acid there was obtained t-butyl [2-(thiazole-4-carboxamido)ethyl]carbamate, m.p. 112°-118°;

starting from 6.55 g of 2-chlorothiazole-4-carboxylic acid there was obtained t-butyl [2-(2-chlorothiazole-4-carboxamido)ethyl]carbamate, m.p. 127°-129°;

starting from 7.0 of 5-bromothiazole-4-carboxylic acid there was obtained t-butyl [2-(5-bromothiazole-4-carboxamido)ethyl]carbamate, m.p. 108°-111°;

starting from 7.3 g of 5-bromo-2-chlorothiazole-4-carboxylic acid there was obtained t-butyl [2-(5-bromo-2-chlorothiazole-4-carboxamido)ethyl]carbamate, m.p. 142°-144°.

7.0 g of t-butyl [2-(4-nitropyridine-2-carboxamido)ethyl]carbamate were stirred at room temperature with 9 ml of methylene chloride and 9 ml of trifluoroacetic acid. Thereafter, the reaction mixture was concentrated under reduced pressure. The residue was converted with hydrogen chloride in ethanol into the hydrochloride and this was recrystallized from ethanol/ether. There was obtained N-(2-aminoethyl)-4-nitropyridine-2-carboxamide hydrochloride as white crystals, m.p. 193°-194°.

The t-butyl (2-aminoethyl)carbamate used as the starting material in the first paragraph was prepared as follows:

A mixture of 600 ml of ethylenediamine in 3 l of dioxane, 1.5 l of water and 90 g of magnesium oxide was stirred at room temperature under argon. There was added dropwise thereto within 20 minutes a solution of 327 g of di-t-butyl dicarbonate in 1.5 l of dioxane. The reaction mixture was stirred at room temperature for 16 hours, subsequently suction filtered over Dicalit and concentrated under reduced pressure. The sludge-like residue was heated to reflux five times with 500 ml of ether each time and decanted off each time, dried and suction filtered over Dicalit. After concentrating the ethereal solution there remained behind as the residue a yellow oil which was distilled in a high vacuum, whereby there was obtained t-butyl (2-aminoethyl)carbamate as a colorless oil, b.p. 84°-86°/46.5 Pa.

In an analogous manner to that described above, starting from 5.7 g of t-butyl [2-(5-nitro-pyridine-2carboxamido)ethyl]carbamate, m.p. 141°-142°, there was obtained N-(2-aminoethyl)-5-nitropyridine-2-carboxamide hydrochloride, m.p. 249°-250°.

EXAMPLE 3

10 g of 3-bromo-2-pyridinecarboxylic acid 80% (containing 20% of 5-bromo-2-pyridinecarboxylic acid) were heated to reflux for 2 hours in 600 ml of absolute tetrahydrofuran and 8.1 g of 1,1'-carbonyldiimidazole. Thereafter, 8.4 g of t-butyl (2-aminoethyl)carbamate were added thereto and the mixture was heated to reflux for a further 4 hours. The reaction mixture was concentrated under reduced pressure. The residue was partitioned between methylene chloride and water. The combined organic phases were washed with water, dried and concentrated. The residue (9.7 g) was chromatographed on silica gel with methylene chloride and mixtures of methylene chloride and ethyl acetate (7:3 and 6:4) as the elution agent. The fractions containing the desired product were pooled and evaporated, and the residue was recrystallized from ethyl acetate/n-hexane. There was obtained t-butyl [2-(3-bromopyridine-2-carboxamido)ethyl]- carbamate as white crystals, m.p. 125°-130°.

3.2 g of t-butyl [2-(3-bromopyridine-2-carboxamido)ethyl]carbamate were heated to reflux for 4 hours with 3.5 ml of methylene chloride and 3.5 ml of trifluoroacetic acid. The reaction mixture was concentrated under reduced pressure, the residue was dissolved in ethanol and the solution was treated with an equimolar amount of ethanolic hydrochloric acid. The hydrochloride was recrystallized from methanol/ether, whereby there was obtained N-(2-aminoethyl)-3-bromopyridine-2-carboxamide hydrochloride as white crystals, m.p. 279°.

The 3-bromo-2-pyridinecarboxylic acid 80% used as the starting material was prepared by the oxidation of 3-bromo-2-methylpyridine in accordance with R. Graf, J. Prakt. Chem. 133 (1932), 33, which in turn was prepared according to J. Abblard, Bull. Soc. Chim. France (1972), 2466.

In an analogous manner to that described above, starting from 4.4 g of t-butyl [2-(4-bromopyridine-2-carboxamido)ethyl]carbamate, m.p. 134°, there was obtained N-(2-aminoethyl)-4-bromopyridine-2-carboxamide hydrochloride, m.p. 224°-225°;

starting from 9.2 g of t-butyl [2-(5-bromopyridine-2-carboxamido)ethyl]carbamate, m.p. 118°, there was obtained N-(2-aminoethyl)-5-bromopyridine-2-carboxamide hydrochloride, m.p. 220°-221°;

starting from 8.0 g of t-butyl [2-(6-bromopyridine-2-carboxamido)ethyl]carbamate, m.p. 108°-109°, there was obtained N-(2-aminoethyl)-6-bromopyridine-2-carboxamide hydrochloride, m.p. 214°-215°.

EXAMPLE 4

8.0 g of 4-chloro-2-pyridinecarboxylic acid were reacted with t-butyl (2-aminoethyl)carbamate in an analogous manner to that described in Example 3. The residue (12.6 g) obtained after working-up was recrystallized from ethyl acetate/n-hexane, whereby there was obtained t-butyl [2-(4-chloropyridine-2-carboxamido)ethyl]carbamate as beige crystals, m.p. 120°-123°.

10.6 g of t-butyl [2-(4-chloropyridine-2-carboxamido)ethyl]carbamate were reacted with trifluoroacetic acid in an analogous manner to that described in Example 3, paragraph 2. The residue was converted into the hydrochloride which was recrystallized from methanol/ether, whereby there was obtained N-(2-aminoethyl)-4-chloropyridine-2-carboxamide hydrochloride as beige crystals, m.p. 228°-229°.

The 4-chloro-2-pyridinecarboxylic acid used as the starting material was prepared according to E. Matsumura et al., Bull. Chem. Soc. Jap., 43 (1970), 3210.

In a analogous manner to that described above,
starting from 10.5 g of t-butyl [2-(6-chloropyridine-2-carboxamido)ethyl]carbamate, m.p. 114°-115°, there was obtained N-(2-aminoethy)-6-chloropyridine-2-carboxamide hydrochloride, m.p. 223°–224°;

starting from 1.7 g of t-butyl [2-(4.6-dichloropyridine-2-carboxamido)ethyl]carbamate, m.p. 126°–127°, there was obtained N-(2-aminoethyl)-4,6-dichloropyridine-2-carboxamide hydrochloride, m.p. 197°–199°;

starting from 1.6 g of t-butyl [2-(5-chloropyridine-2-carboxamido)ethyl]carbamate, m.p. 104°–105°, there was obtained N-(2-aminoethyl)-5-chloropyridine-2-carboxamide hydrochloride, m.p. 193°–195°.

The 5-chloro-2-pyridinecarboxylic acid used as the starting material was prepared according to J. Oehlke et al., Pharmazie 38 (9) (1983), 591 and R. Graf. J. Prakt. Chemie 133 (1932), 31.

EXAMPLE 5

40.4 g of 3-benzyloxy-2-pyridinecarboxylic acid hydrochloride sesquihydrate and 30.0 g of 1,1'-carbonyldiimidazole were stirred at 70° for 1 hour in 600 ml of tetrahydrofuran. To this solution there were then added dropwise 29.7 g of N-(t-butoxycarbonyl)ethylenediamine in 100 ml of tetrahydrofuran and the mixture was left to stir at 70 ° for a further 2 hours.

The reaction mixture was subsequently cooled to room temperature and concentrated to about ¼ of the volume on a rotary evaporator under reduced pressure, taken up in water and extracted three times with chloroform. The chloroform extracts, dried over magnesium sulfate, were evaporated completely and the residue was recrystallized from chloroform/n-hexane, whereby there was obtained t-butyl [2-(3-benzyloxypyridine-2-carboxamido)ethyl]carbamate, m.p. 145°–147°.

A solution of 8.0 g of t-butyl [2-(3-benzyloxypyridine-2-carboxamido)ethyl]carbamate in 100 ml of trifluoroacetic acid was stirred at 20° for ½ hour. The mixture was thereafter evaporated to dryness on a rotary evaporator, the residue was dissolved in ethanol and the solution was treated with hydrogen chloride in methanol (6N). After recrystallization from methanol/ethanol there was obtained N-(2-aminoethyl)-3-benzyloxypyridine-2-carboxamide dihydrochloride, m.p. 139°–142°.

In an analogous manner to that described above, starting from 2.25 g of t-butyl [2-(3-chloro-5-benzyloxypyridine-2-carboxamido)ethyl]carbamate, m.p. 127°–130°, there was obtained N-(2-aminoethyl)-3-chloro-5-benzyloxypyridine-2-carboxamide hydrochloride, m.p. 223°–225°.

starting from 2.0 g of t-butyl [2-(3-{4-chlorobenzyloxy} pyridine -2-carboxamido)-ethyl]carbamate there was obtained N-(2-aminoethyl)-3-(4-chlorobenzyloxy)-pyridine-2-carboxamide dihydrochloride, m.p. 152°–154°;

starting from 3.8 g of t-butyl [2-(3-{4-methylbenzyloxy} pyridine-2-carboxamido)ethyl]carbamate, m.p. 139°–141°, there was obtained N-(2-aminoethyl)-3-(4-methylbenzyloxy)pyridine-2-carboxamide dihydrochloride, m.p. 227°–228°;

starting from 5.0 g of t-butyl [2-(3-benzyloxy-6methyl-pyridine-2-carboxamido)ethyl]carbamate, m.p. 145°–150°, there was obtained N-(2-aminoethyl)-3-benzyloxy-6-methylpyridine-2-carboxamide dihydrochloride, m.p. 174°–175°.

EXAMPLE 6

8.0 g of 3-phenoxy-2-pyridinecarboxylic acid were reacted with t-butyl (2-aminoethyl)carbamate in an analogous manner to that described in Example 3. The residue (12 g) obtained after working-up was recrystallized from ether, whereby there was obtained t-butyl [2-(3-phenoxypyridine-2-carboxamido)ethyl]carbamate as white crystals, m.p. 97°–98°.

8.7 g of t-butyl [2-(3-phenoxypyridine-2-carboxamido)ethyl]carbamate were reacted with trifluoroacetic acid in an analogous manner to that described in Example 3, paragraph 2. The residue was converted into the hydrochloride which was recrystallized twice from ethanol/ether, whereby there was obtained N-(2-aminoethyl)-3-phenoxypyridine-2-carboxamide hydrochloride as white crystals, m.p. 180°–186°.

The 3-phenoxy-2-pyridinecarboxylic acid used as the starting material was prepared by saponifying 3-phenoxy-2-pyridinecarbonitrile with potassium hydroxide in n-butanol. The 3-phenoxy-2-pyridinecarbonitrile was obtained, in turn, according to U.S. Pat. No. 4,212,980, m.p. 120°–121° (from ethyl acetate/n-hexane).

In an analogous manner to that described above, starting from 5.0 g of 3-(2-chlorophenoxy) pyridine-2-carboxylic acid there was obtained t-butyl [2-(3-(2-chlorophenoxy)pyridine -2-carboxamido)ethyl]carbamate, m.p. 86°–87°, which, in turn, was converted into N-(2-aminoethyl)-3-(2-chlorophenoxy)pyridine-2-carboxamide hydrochloride (1.3 mol), white crystals, m.p. 117°–123°;

starting from 5.0 g of 3-(3-chlorophenoxy)-pyridine-2-carboxylic acid there was obtained t-butyl [2-(3-(3-chlorophenoxy)pyridine-2-carboxamido)ethyl]carbamate, m.p. 86°–87°, which, in turn, was converted into N-(2-aminoethyl)-3-(3-chlorophenoxy)pyridine-2-carboxamide hydrochloride, white crystals (alcohol), m.p. 160°–161°;

starting from 5.0 g of 3-(4-chlorophenoxy)pyridine-2-carboxylic acid there was obtained t-butyl [2-(3-(4-chlorophenoxy)pyridine-2-carboxamido)ethyl]carbamate, m.p. 120°–122°, which, in turn, was converted into N-(2-aminoethyl)-3-(4-chlorophenoxy)pyridine-2-carboxamide hydrochloride (1.8 mol), white crystals (alcohol), m.p. 226°–229°;

starting from 5.0 g of 3-(3-methoxyphenoxy)pyridine-2-carboxylic acid there was obtained t-butyl [2-(3-(3-methoxyphenoxy)pyridine-2-carboxamido)ethyl]carbamate, m.p. 81°–82°, which, in turn, was converted into N-(2-aminoethyl)-3-(3-methoxyphenoxy)pyridine-2-carboxamide hydrochloride, white crystals (alcohol/ether), m.p. 142°–143°.

The substituted 3-phenoxy-2-pyridinecarboxylic acids used as the starting materials were prepared by saponifying the correspondingly substituted 3-phenoxy-2-pyridinecarbonitriles with potassium hydroxide in n-butanol. The correspondingly substituted 3-phenoxy-2-pyridinecarbonitriles were obtained, in turn, according to U.S. Pat. No. 4,212,980:

3-(2-chlorophenoxy)pyridine-2-carboxylic acid, m.p. 122°–123° (ethyl acetate/n-hexane);

3-(3-chlorophenoxy)pyridine-2-carboxylic acid, m.p 126°–127° (ethyl acetate/n-hexane);

3-(4-chlorophenoxy)pyridine-2-carboxylic acid, m.p. 136°–137° (ethyl acetate/n-hexane) and 3-(3-methoxyphenoxy)pyridine-2-carboxylic acid, m.p. 126° (ethyl acetate/n-hexane).

EXAMPLE 7

4.0 g of 3-ethoxy-2-pyridinecarboxylic acid and 4.1 g of 1,1'-carbonyldiimidazole were stirred at 70° for 2 hours in 250 ml of tetrahydrofuran. To this solution were then added dropwise 4.1 g of N-(t-butoxycarbonyl)ethylenediamine in 20 ml of tetrahydrofuran and the mixture was left to stir at 70° for a further 2 hours.

The reaction mixture was subsequently cooled to room temperature and concentrated to about ¼ of the volume on a rotary evaporator under reduced pressure, taken up in water and extracted three times with chloroform. The chloroform extracts, dried over magnesium sulfate, were evaporated completely, and the residue was chromatographed on silica gel with 2–5% methanol in methylene chloride as the elution agent and crystallized from methylene chloride/n-hexane, whereby there was obtained t-butyl [2-(3-ethoxypyridine-2-carboxamido)ethyl]carbamate, m.p. 125°–126°.

A solution of 5.1 g of t-butyl [2-(3-ethoxypyridine-2-carboxamido)ethyl]carbamate in 45 ml of trifluoroacetic acid was stirred at 0° for 1 hour. The mixture was thereafter evaporated to dryness on a rotary evaporator, the residue was dissolved in ethanol and treated with hydrogen chloride in ethanol (6N). After recrystallization from ethanol/diethyl ether there was obtained N-(2-aminoethyl)-3-ethoxypyridine-2-carboxamide dihydrochloride, m.p. 188°–190°.

In an analogous manner to that described above, starting from 0.7 g of t-butyl [2-(3-methoxypyridine-2-carboxamido)ethyl]carbamate, m.p. 115°, there was obtained N-(2-aminoethyl)-3-methoxypyridine-2-carboxamide dihydrochloride, m.p. 181°–183°;

starting from 5.3 g of t-butyl [2-(4-methoxypyridine-2-carboxamido)ethyl]carbamate, m.p. 106°–107°, there was obtained N-(2-aminoethyl)-4-methoxypyridine-2-carboxamide dihydrochloride, m.p. 209°–211°;

starting from 1.7 g of 6-methoxy-2-pyridinecarboxylic acid there was obtained t-butyl [2-(6-methoxypyridine-2-carboxamido)ethyl]carbamate, m.p. 104°–105°, which, in turn, was converted into N-(2-aminoethyl)-6-methoxypyridine-2-carboxamide hydrochloride, white crystals (alcohol/ether), m.p. 124°–125°.

The 6-methoxy-2-pyridinecarboxylic acid used as the starting material was prepared according to E. V. Brown and M. B. Shamhu, J. Org. Chem., 36 (14) (1971) 2002, m.p. 129°–130°.

EXAMPLE 8

4.4 g of 3-methyl-2-pyridinecarboxylic acid and 4.4 g of 1,1'-carbonyldiimidazole were stirred at 70° for 3 hours in 300 ml of tetrahydrofuran. To this solution were then added dropwise 8.6 g of N-(t-butoxycarbonyl)ethylenediamine in 50 ml of tetrahydrofuran and the mixture was left to stir at 70° for a further 3 hours.

The reaction mixture was subsequently cooled to room temperature and concentrated to about ¼ of the volume on a rotary evaporator under reduced pressure, taken up in water and extracted three times with chloroform. The chloroform extracts, dried over magnesium sulfate, were evaporated completely and the residue was crystallized from diisopropyl ether, whereby there was obtained t-butyl [2-(3-methylpyridine-2-carboxamido)ethyl]carbamate, m.p. 81°–82°.

A solution of 5.0 g of t-butyl [2-(3-methylpyridine-2-carboxamido)ethyl]carbamate in 50 ml of trifluoroacetic acid was stirred at 20° for 1 hour. The mixture was thereafter evaporated to dryness on a rotary evaporator, the residue was dissolved in methanol and the solution was treated with hydrogen chloride in methanol (6N). After recrystallization from methanol/diethyl ether there was obtained N-(2-aminoethyl)-3-methylpyridine-2-carboxamide hydrochloride, m.p. 254°–256°.

In an analogous manner to that described above, starting from 2.0 g of t-butyl [2-(6-methylpyridine-2-carboxamido)ethyl]carbamate, m.p. 94°–95° there was obtained N-(2-aminoethyl)-6-methylpyridine-2-carboxamide dihydrochloride, m.p. 218°–222°.

EXAMPLE 9

10.0 g of 3-methyl-4-nitro-2-pyridinecarboxylic acid were reacted with t-butyl (2-aminoethyl)carbamate in an analogous manner to that described in Example 2. The residue (17.8 g) obtained after working-up was recrystallized from ethyl acetate, whereby there was obtained t-butyl [2-(3-methyl-4-nitropyridine-2-carboxamido)ethyl]carbamate as white crystals, m.p. 133°–134°.

14.6 g of t-butyl [2-(3-methyl-4-nitropyridine-2-carboxamido)ethyl]carbamate were reacted with trifluoroacetic acid in an analogous manner to that described in Example 2, paragraph 2. The residue was converted into the hydrochloride which was recrystallized from methanol/ether, whereby there was obtained N-(2-aminoethyl)-3-methyl-4-nitropyridine-2-carboxamide hydrochloride as white crystals, m.p. 204°–205°.

The 3-methyl-4-nitro-2-pyridinecarboxylic acid used as the starting material was prepared according to E. Matsumara et al., Bull. Chem. Soc. Jap. 43 (1970) 3210.

EXAMPLE 10

9.2 g of 4-chloro-3-methyl-2-pyridinecarboxylic acid were reacted with t-butyl (2-aminoethyl)carbamate in an analogous manner to that described in Example 2. The residue (14.7 g) obtained after working-up was recrystallized from ethyl acetate, whereby there was obtained t-butyl [2-(4-chloro-3-methylpyridine-2-carboxamido)ethyl]carbamate as white crystals, m.p. 134°–135°.

12.5 g of t-butyl [2-(4-chloro-3-methylpyridine-2-carboxamido)ethyl]carbamate were reacted with trifluoroacetic acid in an analogous manner to that described in Example 2, paragraph 2. The residue was converted into the hydrochloride which was recrystallized from ethanol/ether, whereby there was obtained N-(2-aminoethyl)-4-chloro-3-methylpyridine-2-carboxamide hydrochloride as white crystals, m.p. 180°–181°.

The 4-chloro-3-methyl-2-pyridinecarboxylic acid used as the starting material was prepared according to E. Matsumura et al., Bull. Chem. Soc. Jap., 43 (1970), 3210.

In analogous manner, from 3.3 g of 4-chloro-5-methoxy-2-pyridinecarboxylic acid there was obtained t-butyl [2-(4-chloro-5-methoxypyridine-2-carboxamido)ethyl]carbamate as pale yellow crystals (ethyl acetate/n-hexane), m.p. 132°–133°, which, in turn, was converted into N-(2-aminoethyl)-4-chloro-5-methoxypyridine-2-carboxamide hydrochloride, white crystals (methanol/ether), m.p. 256°–257°.

The 4-chloro-5-methoxy-2-pyridinecarboxylic acid used as the starting materials was prepared as follows:

Kojic acid (5-hydroxy-2-hydroxymethyl-4H-pyran-4-one) was methylated according to K. N. Campbell et al., J. Org. Chem., 15 (1950), 221, to give 2-hydroxymethyl-5-methoxy-4H-pyran-4-one which was then converted according to J. W. Armit and T. J. Nolan, J. Chem. Soc. (1931), 3023, into 2-hydroxymethyl-5-methoxy-4-pyridone. This was oxidized with nitric acid according to K. Heyns and G. Vogelsang, Ber., 87 (1954), 13, to give 5-methoxy-pyridone-(4)carboxylic acid-(2) which was thereafter boiled with thionyl chloride and subsequently saponified. 4-Chloro-5-methoxy-2-pyridinecarboxylic acid was obtained as orange crystals, m.p. 209°.

EXAMPLE 11

5.5 g of 3-aminopyridine-2-carboxylic acid and 6.8 g 1,1'-carbonyldiimidazole were stirred at 70° for 1 hour in 120 ml of tetrahydrofuran. To this solution was then added dropwise 6.75 g of N-(t-butoxycarbonyl)ethylenediamine in 10 ml of tetrahydrofuran and the mixture was left to stir at 70° for a further 2 hours.

The reaction mixture was subsequently cooled to room temperature and concentrated to about ¼ of the volume on a rotary evaporator under reduced pressure, taken up in water and extracted three times with chloroform. The chloroform extracts, dried over magnesium sulfate, were evaporated completely and the residue was chromatographed on silica gel with chloroform as the elution agent. There was obtained t-butyl [2-(3-aminopyridine-2-carboxamido)ethyl]carbamate, m.p. 103°-105°.

A solution of 2.8 g of t-butyl [2-(3-aminopyridine-2-carboxamido)ethyl]carbamate in 50 ml of trifluoroacetic acid was stirred at 0° for 1 hour. The mixture was thereafter evaporated to dryness on a rotary evaporator, the residue was dissolved in methanol and the solution was treated with hydrogen chloride in methanol (6N). After recrystallization from methanol/diethyl ether there was obtained N-(2-aminoethyl)-3-aminopyridine-2-carboxamide dihydrochloride, m.p. 222°-225°.

EXAMPLE 12

4.9 g of N-(2-aminoethyl)-3-benzyloxypyridine-2-carboxamide dihydrochloride were hydrogenated in 70 ml of a 1:1 mixture of ethanol and water with 0.5 g of palladium-on-active carbon (10% Pd) for 1 hour at 20° and normal pressure. The catalyst was subsequently filtered off, the filtrate was concentrated on a rotary evaporator under reduced pressure to half volume, whereupon N-(2-aminoethyl)-3-hydroxy-2-pyridinecarboxamide dihydrochloride crystallized out after the addition of diethyl ether, m.p. 256°-258°.

In an analogous manner, starting from 0.6 g of N-(2-aminoethyl)-3-benzyloxy-6-methylpyridine-2-carboxamide dihydrochloride, m.p. 174°-175°. (Example 5), there was obtained N-(2-aminoethyl)-3-hydroxy-6-methylpyridine-2-carboxamide dihydrochloride, m.p. 237°-243°.

EXAMPLE 13

A solution of 1.95 g of t-butyl [2-(3-benzyloxy-5-chloropyridine-2-carboxamido)ethyl]carbamate, m.p. 130°-133°, in 30 ml of trifluoroacetic acid was stirred at 50° for 7 hours. The mixture was thereafter evaporated to dryness on a rotary evaporator, the residue was dissolved in methanol and the solution was treated with hydrogen chloride in methanol (6N). After recrystallization from methanol there was obtained N-(2-aminoethyl)-3-hydroxy-5-chloropyridine-2-carboxamide hydrochloride, m.p. 220°-223°.

EXAMPLE 14

A solution of 25.0 g of pyrazinecarboxylic acid in 300 ml of methylene chloride and 20.1 ml of ethyl chloroformate was treated dropwise at 0° within ½ hour with 31 ml of triethylamine. After ½ hour the solution obtained was added dropwise at 0° to 68 ml of ethylenediamine in 200 ml of methylene chloride and the mixture was left to stir further for 1 hour without external cooling. Thereafter, the precipitated material was filtered off and the filtrate was evaporated to dryness on a rotary evaporator under reduced pressure. The residue was recrystallized twice from isopropanol, whereby there was obtained N-(2-aminoethyl)pyrazine-2-carboxamide hydrochloride, m.p. 205°-207°.

EXAMPLE 15

2.1 g of 5-chloropyrazine-2-carboxylic acid and 2.3 g of 1,1'-carbonyldiimidazole were stirred at 70° for ¾ hours in 10 ml of tetrahydrofuran. To this solution were then added dropwise 2.2 g of N-(t-butoxycarbonyl)ethylenediamine in 5 ml of tetrahydrofuran and the mixture was left to stir at 70° for a further hour.

The reaction mixture was subsequently cooled to room temperature and concentrated on a rotary evaporator under reduced pressure, dissolved in dilute hydrochloric acid (0.1N) and extracted three times with methylene chloride. The methylene chloride extracts, dried over magnesium sulfate, were evaporated completely and the residue was chromatographed on silica gel with methylene chloride as the elution agent, whereby there was obtained t-butyl [2-(5-chloropyrazine-2-carboxamido)ethyl]carbamate.

A solution of 1.6 g of t-butyl [2-(5-chloropyrazine-2-carboxamido)ethyl]carbamate in 6 ml of trifluoroacetic acid was stirred at 20° for 20 minutes. The mixture was thereafter evaporated to dryness on a rotary evaporator, the residue was dissolved in methanol and the solution was treated with hydrogen chloride in methanol (6N). After recrystallization from methanol/diethyl ether there was obtained N-(2-aminoethyl)-5-chloropyrazine-2-carboxamide hydrochloride, m.p. 225°.

EXAMPLE 16

21.0 g of 5-bromo-2-furancarboxylic acid were suspended in 650 ml of toluene and 40 ml of thionyl chloride and the suspension was heated to reflux for 2 hours. The reaction solution was thereafter concentrated, whereby 5-bromo-2-furancarboxylic acid chloride was obtained as the residue.

A solution of 22.6 g of 5-bromo-2-furancarboxylic acid chloride in 100 ml of methylene chloride was added dropwise within 20 minutes at 0°-8° to a solution, pre-cooled to 0°, of 11.0 g of monoacetyl-ethylenediamine in 250 ml of methylene chloride and 18 ml of triethylamine. The reaction mixture was stirred at room temperature overnight, suction filtered and washed with methylene chloride. There was obtained N-(2-acetamino ethyl)-5-bromo-2-furancarboxamide as pale beige crystals, m.p. 175°-176°.

22.2 g of N-(2-acetaminoethyl)-5-bromo-2-furancarboxamide, 150 ml of ethanol and 160 ml of 2N hydrochloric acid were heated to reflux for 22 hours. The reaction mixture was thereafter concentrated under reduced pressure. There were obtained 214 g of beige crystals which were heated to reflux in a mixture of 750 ml of ethanol and 100 ml of methanol. The suspension was thereafter adjusted to pH 2 with ethanolic hydrochloric acid and filtered. The filtrate was concentrated to a volume of about 300 ml under reduced pressure, whereby crystallization took place. The mixture was cooled to 5° and the crystallizate was filtered off under suction. After drying there was obtained 5-bromo-N-(2- aminoethyl)-2-furancarboxamide hydrochloride as pale beige crystals, m.p. 174°-175°.

EXAMPLE 17

In an analogous manner to that described in Example 16, from 43 g of 5-bromo-2-thiophenecarboxylic acid there were obtained white crystals which were heated to reflux in 500 ml of ethanol and cooled at 2° overnight. After suction filtration and drying there was obtained N-(2-acetaminoethyl)-5-bromo-2-thiophenecarboxamide as white crystals, m.p. 244°-245°.

N-(2-Acetaminoethyl)-5-bromo-2-thiophenecarboxamide was reacted with hydrochloric acid in an analogous manner to that described in Example 1, paragraph 3. The residue was dissolved in alcohol (pH 1), filtered and concentrated to about 300 ml under reduced pressure. After cooling to 5° the product was filtered off under suction and dried, whereby 5-bromo-N-(2-aminoethyl)-2-thiophenecarboxamide hydrochloride was obtained as white crystals, m.p. 221°-222°, after recrystallization from ethanol.

EXAMPLE 18

10.0 g of 5-methyl-2-thiophenecarboxylic acid were reacted with t-butyl (2-aminoethyl)carbamate in an analogous manner to that described in Example 2. After workingup there was obtained as the residue a yellowish oil (20.6 g) which was dissolved in ethyl acetate and filtered over 100 g of silica gel. The pure fractions were combined and concentrated. The residue (15.9 g of an oil) was crystallized from ethyl acetate/n-hexane, whereby there was obtained t-butyl [2-(5-methylthiophene-2-carboxamido)ethyl]carbamate as white crystals, m.p. 109°-110°.

14.9 g of t-butyl [2-(5-methylthiophene-2-carboxamido)ethyl]carbamate were reacted with trifluoroacetic acid in an analogous manner to that described in Example 2, paragraph 2. The residue was converted into the hydrochloride which was recrystallized from ethanol/ether, whereby there was obtained N-(2-aminoethyl)-5-methylthiophene-2-carboxamide hydrochloride as light beige crystals, m.p. 161°-162°.

EXAMPLE 19

3.1 g of 5-methyloxazole-4-carboxylic acid and 4.0 g of 1,1'-carbonyldiimidazole were stirred at 70° for 1 hour in 30 ml of tetrahydrofuran. To this solution were then added dropwise 3.9 g of N-(t-butoxycarbonyl)ethylenediamine in 15 ml of tetrahydrofuran and the mixture was left to stir at 20° for a further ½ hour.

The reaction mixture was subsequently cooled to room temperature and concentrated to about ¼ of the volume on a rotary evaporator under reduced pressure, taken up in water and extracted three times with chloroform. The chloroform extracts, dried over magnesium sulfate, were evaporated completely and the residue was crystallized from chloroform/n-hexane, whereby there was obtained t-butyl [2-(5-methyloxazole-4-carboxamido)ethyl]carbamate.

A solution of 4.5 g of t-butyl [2-(5-methyloxazole-4-carboxamido)ethyl]carbamate in 20 ml of trifluoroacetic acid was stirred at 20° for ¼ hour. The mixture was thereafter evaporated to dryness on a rotary evaporator, the residue was taken up in methanol and the solution was treated with hydrogen chloride in methanol (6N). After recrystallization from methanol there was obtained N-(2-aminoethyl)-5-methyloxazole-4-carboxamide hydrochloride, m.p. 225°.

In an analogous manner to that described above, starting from 9.6 g of t-butyl [2-(oxazole-4-carboxamido)ethyl]carbamate, m.p. 148°-150°, there was obtained N-(2-aminoethyl)oxazole-4-carboxamide hydrochloride, m.p. 222°-224°.

EXAMPLE 20

9.8 g of thiazole-2-carboxylic acid and 12.3 g of 1,1'-carbonyldiimidazole were stirred at 70° for 1 hour in 35 ml of tetrahydrofuran. To this solution were then added dropwise 12.2 g of N-(t-butoxycarbonyl)ethylenediamine in 20 ml of tetrahydrofuran and the mixture was left to stir at 70° for a further ½ hour.

The reaction mixture was subsequently cooled to room temperature and concentrated to about ¼ of the volume on a rotary evaporator under reduced pressure, taken up in water and extracted three times with ethyl acetate. The ethyl acetate extracts, dried over magnesium sulfate, were evaporated completely, whereby t-butyl [2-(thiazole-2-carboxamido)ethyl]carbamate was obtained.

A solution of 16.5 g of t-butyl [2-(thiazole-2-carboxamido)ethyl]carbamate in 50 ml of trifluoroacetic acid was stirred at 20° for ½ hour. The mixture was thereafter evaporated to dryness on a rotary evaporator, the residue was taken up in methanol and the solution was treated with hydrogen chloride in methanol (6N). After recrystallization from methanol there was obtained N-(2-aminoethyl)thiazole-2-carboxamide hydrochloride, m.p. 220°.

In an analogous manner to that described above,
starting from 11.8 g of t-butyl [2-(thiazole-4-carboxamido)ethyl]carbamate, m.p. 112°-118°, there was obtained N-(2-aminoethyl)thiazole-4-carboxamide dihydrochloride, m.p. 206°-209°;
starting from 9.15 g of t-butyl [2-(2-chlorothiazole-4-carboxamido)ethyl]carbamate, m.p. 127°-129°, there was obtained N-(2-aminoethyl)-2-chlorothiazole-4-carboxamide hydrochloride, m.p. 158°-160°;
starting from 7.0 g of t-butyl [2-(5-bromothiazole-4-carboxamido)ethyl]carbamate, m.p. 108°-111°, there was obtained N-(2-aminoethyl)-5-bromothiazole-4-carboxamide hydrochloride, m.p. 281°-283°;
starting from 8.7 g of t-butyl [2-(5-bromo-2-chlorothiazole-4-carboxamido)ethyl]carbamate, m.p. 142°-144°, there was obtained N-(2-aminoethyl)-5-bromo-2-chlorothiazole-4-carboxamide hydrochloride, m.p. 222°-225°.

EXAMPLE 21

1.4 g of 5-methylisoxazole-3-carboxylic acid and 1.8 g of 1,1'-carbonyldiimidazole were stirred at 70° for 1 hour in 10 ml of tetrahydrofuran. To this solution were then added dropwise 1.8 g of N-(t-butoxycarbonyl)ethylenediamine in 3.5 ml of tetrahydrofuran and the mixture was left to stir at 20° for a further hour.

The reaction mixture was subsequently cooled to room temperature and concentrated to about ¼ of the volume on a rotary evaporator under reduced pressure, taken up in water and extracted three times with chloroform. The chloroform extracts, dried over magnesium sulfate, were evaporated completely and the residue was crystallized from chloroform/n-hexane, whereby t-butyl [2-(5-methylisoxazole-3-carboxamido)ethyl]carbamate was obtained.

A solution of 2.6 g of t-butyl [2-(5-methylisoxazole--3-carboxamido)ethyl]carbamate in 14 ml of trifluoroacetic acid was stirred at 20° for ½ hour. The mixture was thereafter evaporated to dryness on a rotary evaporator, the residue was taken up in methanol and the solution was treated with hydrogen chloride in methanol (6N). After recrystallization from methanol/diethyl ether there was obtained N-(2-aminoethyl)-5-methylisoxazole-3-carboxamide hydrochloride, m.p. 208°.

EXAMPLE 22

10.0% of pyridine-2-carboxylic acid were suspended in 150 ml of toluene and the suspension was heated to reflux for 2 hours with 17.7 ml of thionyl chloride and 3 drops of dimethylformamide. Thereafter, the mixture was evaporated to dryness under reduced pressure, the residue was treated with toluene and again evaporated to dryness. There was obtained picolinic acid chloride as dark green crystals which were used directly in the next step.

15.4 ml of ethanolamine were placed under argon with 30 ml of dimethylformamide and cooled to 0°–5°. A solution of 11.3 g of picolinic acid chloride in 100 ml of dimethylformamide was added dropwise thereto at 0°–10° and the mixture was stirred at room temperature overnight. The dimethylformamide was distilled off under reduced pressure. The residue was dissolved in methylene chloride and separated from the insoluble constituents, and thereafter chromatographed on silica gel; elution agent: methylene chloride, thereafter methylene chloride/methanol (9:1). N-(2-Hydroxyethyl)-pyridine-2-carboxamide was obtained as a yellow oil.

3.0 g of N-(2-hydroxyethyl)pyridine-2-carboxamide were placed in a round flask with 20 ml of methylene chloride and 2.5 ml of triethylamine and the mixture was cooled to 0°–5°. A solution of 1.4 ml of methanesulfochloride in 30 ml of methylene chloride was added dropwise thereto while cooling well at 0°–5°. The reaction mixture was stirred at 0°–5° for a further 2 hours and thereafter added dropwise at 0°–5° to 30 ml of concentrated (25%) ammonia. The reaction mixture was stirred at room temperature overnight and thereafter concentrated under reduced pressure. The residue was dissolved in methylene chloride, extracted with 2N hydrochloric acid and washed with water. The aqueous extracts were combined, made basic with concentrated (28%) sodium hydroxide solution and extracted 3 times with methylene chloride. The organic extracts were dried over magnesium sulfate, filtered and evaporated. There was obtained a yellow oil which was chromatographed on silica gel for further purification. As the elution agent there was used firstly ethyl acetate, thereafter an ethyl acetate/alcohol mixture and finally alcohol. There was obtained N-(2-aminoethyl)pyridine-2-carboxamide which, in accordance with thin-layer chromatography, was identical with the compound described in Example 1.

EXAMPLE A

Interlocking gelatine capsules of 5 mg

| Composition | |
|---|---|
| 1. N—(2-Aminoethyl)-4-bromopyridine-2-carboxamide hydrochloride | 5.75 mg* |
| 2. Lactose powder | 80.25 mg |
| 3. Maize starch | 40.00 mg |
| 4. Talc | 3.60 mg |
| 5. Magnesium stearate | 0.40 mg |
| 6. Lactose crystals | 110.00 mg |
| Capsule fill weight | 240.00 mg |

*corresponding to 5 mg of base

Manufacturing procedure:

1–5 are mixed and sieved through a sieve having a mesh size of 0.5 mm. Thereafter, 6 is admixed and the mixture is mixed. This finished mixture is filled into interlocking gelatine capsules of suitable size (e.g. No. 2) having an individual fill weight of 240 mg.

EXAMPLE B

Tablets of 5 mg

| Composition | |
|---|---|
| 1. N—(2-Aminoethyl)-4-bromopyridine-2-carboxamide hydrochloride | 5.75 mg* |
| 2. Lactose powder | 104.25 mg |
| 3. Maize starch | 45.00 mg |
| 4. Polyvinylpyrrolidine K 30 | 15.00 mg |
| 5. Maize starch | 25.00 mg |
| 6. Talc | 4.50 mg |
| 7. Magnesium stearate | 0.50 mg |
| Tablet Weight | 200.00 mg |

*corresponding to 5 mg of base

Procedure:

1–3 are mixed and sieved through a sieve having a mesh size of 0.5 mm. This powder mixture is moistened with an alcoholic solution of 4 and kneaded. The moist mass is granulated, dried and converted to a suitable particle size, 5,6 and 7 are added in succession to the dried granulate and the mixture is mixed. The finished press mixture is pressed to tablets of suitable size having an individual weight of 200 mg.

EXAMPLE C

Interlocking gelatine capsules of 10 mg

| Composition | |
|---|---|
| 1. N—(2-Aminoethyl)-4-chloropyridine-4-carboxamide hydrochloride | 11.82 mg* |
| 2. Lactose powder | 74.18 mg |
| 3. Maize starch | 40.00 mg |
| 4. Talc | 3.60 mg |
| 5. Magnesium stearate | 0.40 mg |
| 6. Lactose crystals | 110.00 mg |
| Capsule fill weight | 240.00 mg |

*corresponding to 10 mg of base

Manufacturing procedure:

1–5 are mixed and sieved through a sieve having a mesh size of 0.5 mm. Thereafter, 6 is and mixed and the mixture is mixed. This finished mixture is filled into interlocking gelatine capsules of suitable size (e.g. No. 2) having an individual fill weight of 240 mg.

EXAMPLE D

Tablets of 10 mg

| Composition: | |
|---|---|
| 1. N—(2-Aminoethyl)-4-chloropyridine-2-carboxamide hydrochloride | 11.82 mg* |
| 2. Lactose powder | 103.18 mg |
| 3. Maize starch | 40.00 mg |
| 4. Polyvinylpyrrolidone K 30 | 15.00 mg |
| 5. Maize starch | 25.00 mg |

| -continued | |
|---|---|
| Composition: | |
| 6. Talc | 4.50 mg |
| 7. Magnesium stearate | 0.50 mg |
| Tablet weight | 200.00 mg |

*corresponding to 10 mg of base

Procedure:

1–3 are mixed and sieved through a sieve having a mesh size of 0.5 mm. This powder mixture is moistened with an alcoholic solution of 4 and kneaded. The moist mass is granulated, dried and converted to a suitable particle size, 5,6 and 7 are added in succession to the dried granulate and the mixture is mixed. The finished mixture is pressed to tablets of suitable size having an individual weight of 200 mg.

EXAMPLE E

When the procedures described in Examples A–D are followed, tablets and capsules can be manufactured from the following, likewise preferred compounds:

N-(2-aminoethyl)-2-chlorothiazole-4-carboxamide hydrochloride,

N-(2-aminoethyl)-3-aminopyridine-2-carboxamide dihydrochloride,

N-(2-aminoethyl)pyridine-2-carboxamide dihydrochloride and

N-(2-aminoethyl)-5-chloropyridine-2-carboxamide hydrochloride.

We claim:

1. A compound of the formula

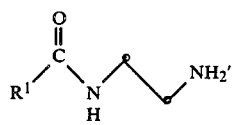

wherein R' is

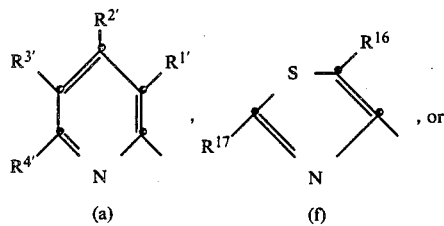

in which at least two of the substituents $R^{1'}$, $R^{2'}$, $R^{3'}$ and $R^{4'}$ are hydrogen and the remaining two each independently are hydrogen, halogen, nitro, amino, hydroxy, lower-alkoxy, lower-alkyl, phenyloxy, phenylmethyloxy, phenyloxy or phenylmethyloxy substituted by one or more substituents selected from the group consisting of halogen, lower-alkyl, lower-alkoxy, nitro and hydroxy with the proviso that $R^{1'}$, $R^{2'}$, $R^{3'}$ and $R^{4'}$ are not simultaneously hydrogen, or a pharmaceutical usable acid addition salt thereof.

2. A compound according to claim 1, wherein R' is the group (a') and three of the substituents $R^{1'}$, $R^{2'}$, $R^{3'}$ and $R^{4'}$ are hydrogen and the fourth substituent is halogen, amino, hydroxy or lower-alkoxy.

3. A compound according to claim 1, wherein R' is the group (f) and one of the substituents $R^{16}$ and $R^{17}$ or $R^{18}$ is hydrogen and the other substituent is hydrogen or halogen.

4. A compound in accordance with claim 1, N-(2-Aminoethyl)-4-methoxypyridine-2-carboxamide or a pharmaceutically usable acid addition salt thereof.

5. A compound in accordance with claim 1, N-(2-aminoethyl)-4-bromopyridine-2-carboxamide or a pharmaceutically usable acid addition salt thereof.

6. A compound in accordance with claim 1, N-(2-aminoethyl)-4-chloropyridine-2-carboxamide or a pharmaceutically usable acid addition salt thereof.

7. A compound in accordance with claim 1, N-(2-aminoethyl)-2-chlorothiazole-4-carboxamide or a pharmaceutically usable acid addition salt thereof.

8. A compound in accordance with claim 1, N-(2-aminoethyl)-5-methylisoxazole-3-carboxamide or a pharmaceutically usable acid addition salt thereof.

9. A compound in accordance with claim 1, N-(2-aminoethyl)-6-bromopyridine-2-carboxamide or a pharmaceutically usable acid addition salt thereof.

10. A compound in accordance with claim 1, N-(2-aminoethyl)-6-chloropyridine-2-carboxamide or a pharmaceutically usable acid addition salt thereof.

11. A compound in accordance with claim 1, N-(2-aminoethyl)-5-bromothiazole-4-carboxamide or a pharmaceutically usable acid addition salt thereof.

12. A compound in accordance with claim 1, N-(2-aminoethyl)-3-aminopyridine-2-carboxamide or a pharmaceutically usable acid addition salt thereof.

13. A compound in accordance with claim 1, N-(2-aminoethyl)-5-chloropyridine-2-carboxamide or a pharmaceutically usable acid addition salt thereof.

14. A composition comprising an amount effective for MAO inhibition of a compound of the formula

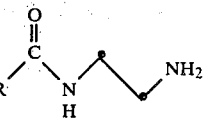

wherein R is

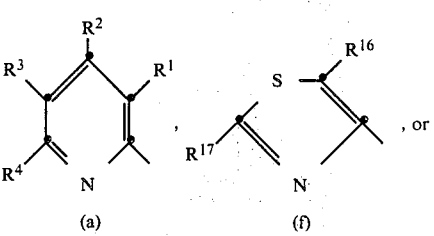

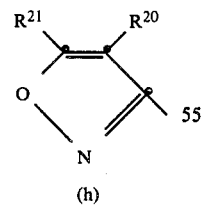

-continued

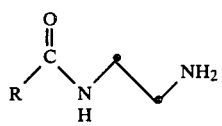

(h)

in which at least two of the substituents $R^1$, $R^2$, $R^3$ and $R^4$ are hydrogen and the remaining two each independently are hydrogen, halogen, nitro, amino, hydroxy, lower-alkoxy, lower-alkyl phenyloxy, phenylmethyloxy, phenyloxy or phenylmethyloxy substituted by one or more substituents selected from the group consisting of halogen, lower-alkyl, lower-alkoxy, nitro and hydroxy $R^{16}$, is hydrogen, halogen or lower-alkyl, and $R^{17}$ is hydrogen or halogen or a pharmaceutical usable acid addition salt thereof.

15. A composition in accordance with claim 14, wherein the compound of formula I is N-(2-aminoethyl)-5-chloropyrididne-2-carboxamide or a pharmaceutically usable acid addition salt thereof.

16. A method for treating depressive states and parkinsonism which comprises administering an amount effective for the treatment of depressive states or parkinsonism of a compound of the formula

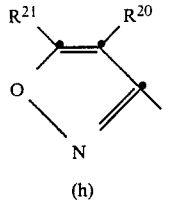

wherein R is

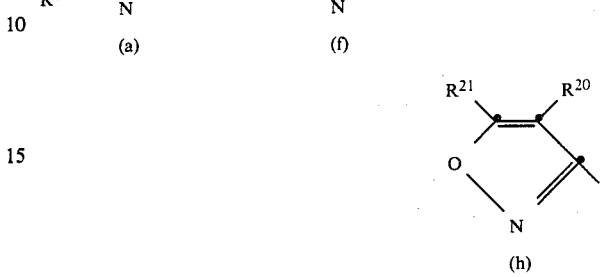

in which at least two of the substituents $R^1$, $R^2$, $R^3$ and $R^4$ are hydrogen and the remaining two each independently are hydrogen, halogen, nitro, amino, hydroxy, lower-alkoxy, lower-alkyl phenyloxy, phenylmethyloxy, phenyloxy or phenylmethyloxy substituted by one or more substituents selected from the group consisting of halogen, lower-alkyl, lower-alkoxy, nitro and hydroxy $R^{16}$ is hydrogen, halogen or lower-alkyl, and $R^{17}$ is hydrogen or halogen or a pharmaceutical usable acid addition salt thereof.

17. A method in accordance with claim 16, wherein the compound of formula I is N-(2-aminoethyl)-5-chloropyridine-2-carboxamide or a pharmaceutically usable acid addition salt thereof.

* * * * *